(12) United States Patent
Hartz

(10) Patent No.: US 7,098,217 B2
(45) Date of Patent: Aug. 29, 2006

(54) 3,7-DIHYDRO-PURINE-2,6-DIONE DERIVATIVES AS CRF RECEPTOR LIGANDS

(75) Inventor: Richard A. Hartz, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 38 days.

(21) Appl. No.: 10/935,961

(22) Filed: Sep. 8, 2004

(65) Prior Publication Data

US 2005/0026937 A1 Feb. 3, 2005

Related U.S. Application Data

(62) Division of application No. 10/289,851, filed on Nov. 7, 2002, now abandoned.

(60) Provisional application No. 60/331,829, filed on Nov. 20, 2001.

(51) Int. Cl.
*A61K 31/522* (2006.01)
(52) U.S. Cl. .......................... 514/263.34; 514/263.35; 514/263.36; 514/263.22
(58) Field of Classification Search .................... None
See application file for complete search history.

(56) References Cited

FOREIGN PATENT DOCUMENTS

| WO | WO 95/10506 | 4/1995 |
|---|---|---|
| WO | WO 97/35846 | 2/1997 |
| WO | WO 97/35539 | 10/1997 |
| WO | WO 97/44308 | 11/1997 |
| WO | WO 98/03510 | 1/1998 |
| WO | WO 99/01439 | 1/1999 |
| WO | WO 99/01454 | 1/1999 |
| WO | WO 99/11643 | 3/1999 |
| WO | WO 99/51608 | 10/1999 |
| WO | WO 00/01675 | 1/2000 |
| WO | WO 00/11003 | 3/2000 |

OTHER PUBLICATIONS

Arato, M., et al., "elevated CSF CRF in suicide victims," *Biol. Psychiatry*, 1989, 25, 355-359.
Banki, C.M., et al., "CSF corticotrophin-releasing factor-like immunoreactivity in depression and schizophrenia," *Am. J. Psychiatry*, 1987, 144, 873-877.
Battaglia, C.W., et al., "Characterization of corticotrophin-releasing factor receptor-mediated adenylate cyclase activity in the rat central nervous system," *SYNAPSE*, 1987, 1, 572-581.
Berridge, C.W., et al., "Corticotropin-releasing factor elicits naloxone sensitive stress-like alterations in exploratory behavior in mice," *Peptides*, 1986, 16, 83-93.
Blalock, J.E., "A molecular basis for bidirectional communication between the immune and neuroendocrine systems," *Physiological Reviews*, 1989, 69(1), 1-32.

Britton, D.R., et al., "Intraventricular corticotrophin-releasing factor enhances behavioral effects of novety," *Life Sci.*, 1982, 31, 363-367.
Britton, K.T., et al., "Chlordiazepoxide attenuates response suppression induced by corticotrophin-releasing factor in the conflict test," *Psychopharmacology*, 1985, 86, 170-174.
Britton, K.T., et al., "Corticotropin releasing factor and amphetamine exaggerate partial agonist properties of benzodiazepine antagonist Ro15-1788 in conflict test," *Psychopharmacology*, 1988, 94, 306-311.
Chrousos, G.P., "The role of stress and the hypothalamic-pituitary-adrenal axis in the pathogenesis of the metabolic syndrome: neuroendocrine and target tissue-related causes," *Int. J. Obesity*, 2000, 24 (Suppl. 2), S50-S55.
De Souza, E.B., et al.(Eds.), Corticotropin-Releasing Factor: Basic and Clinical Studies of a Neuropeptide, CRC Press, 1990, p. 221-224.
De Souza, E.B., et al., "Corticotropin-releasing factor receptors are widely distributed within the rat central nervous system: an autoradiographic study," *J. Neurosci.*, 1985, 5(12), 3189-3203.
De Souza, E.B., "CRH defects in alzheimer's and other neurologic diseases," *Hosp. Practice*, Sep. 15, 1988, 23, 59-71.
Dunn., A.J., et al., "Physiological and behavioral responses to corticotrophin-releasing factor administration: is CRF a mediator of anxiety or stress responses?," *Brain Research Reviews*, 1990, 15, 71-100.
France, R.D., et al., "CSF corticotrophin-releasing factor-like immunoactivity in chronic pain patients with and without major depression," *Biol. Psychiatry*, 1988, 28, 86-88.
Gilligan, P.J., et al., "Corticotropin releasing factor (CRF) receptor modulators: progress and opportunities for new therapeutic agents," *J. Medicinal Chem.*, May 4, 2000, 43(9), 1641-1660.
Gold, P.W., et al., "Psychiatric implications basic and clinical studies with corticotrophin-releasing factor," *Am. J. Psychiatry*, May 1984, 141(5), 619-627.

(Continued)

*Primary Examiner*—Phyllis G. Spivack
(74) *Attorney, Agent, or Firm*—Shah R. Makujina; Woodcock Washburn, LLP

(57) ABSTRACT

3,7-Dihydro-purine-2,6-dione derivatives of Formula (I) are provided

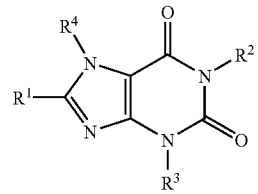

(I)

wherein $R_1$, $R^2$, $R^3$ and $R^4$ are herein defined for use as CRF receptor ligands in the treatment of disorders characterized by overexpression of corticotropin releasing factor (CRF), such as anxiety, depression, and irritable bowel syndrome.

7 Claims, No Drawings

OTHER PUBLICATIONS

Gold, P.W., et al., "Responses to corticotrophin-releasing hormone in the hypercortisolism of depression and cushing's disease," *New Eng. J. Med.*, May 22, 1986, 314(21), 1129-1335.

Greene, et al., Protective Groups in Organic Synthesis, *John Wiley & Sons, Inc.*, 1999.

Grigoriadis, D.E., et al., "Effects of chronic antidepressant and benzodiazepine treatment on corticotrophin-releasing-factor receptors in rat brain and pituitary," *Neuropsychopharmacology*, 1989, 2(1), 53-60.

Holsboer, F., et al., "Acth and multisteroid responses to corticotrophin-releasing factor in depressive illness: relationship to multisteroid responses after acth stimulation and dexamethasone suppression," *Psychoneuroendocrinology*, 1984, 9(2), 147-160.

Koob, G.F., "Neurobiology of addition toward the development of new therapies," *Ann. N.Y. Acad. Sci.*, 2000, 909, 170-185.

Koob, G.F., "Stress, corticotrophin-releasing factor, and behavior," *Persp. Behav. Med.*, 1985, 2, 39-52.

Lam, P.Y.S., et al., "Copper promoted aryl/saturated heterocyclic C-N bond cross-coupling with arylboronic acid and arylstannane," *Synlett.*, 2000, 5, 674-676.

Lewis, R.J. (Ed.), Hawley's Condensed Chemical Dictionary, 13th Ed., *J. Wiley & Sons, Inc., NY*, 1997.

Maillot, C., et al., "Peripheral corticotrophin-releasing factor and stress-stimulated colonic motor activity involve type 1 receptor in rats," *Gastroenterology*, 2000, 119, 1569-1579.

Mastorakos, G., et al., "Maternal hypothalamic-pituitary-adrenal axis in pregnancy and the postpartum period," *Ann. N.Y. Acad. Sci.*, 2000, 900, 95-106.

McCarthy, J.R., et al., "Recent advances with the $CRF_1$ receptor: design of small molecule inhibitors, receptor subtypes and clinical indications," *Curr. Pharm. Res.*, 1999, 5, 289-315.

Morley, J.E., "Minireview, neuropeptides: conductors of the immune orchestra," *Life Sci.*, 1987, 41, 527-544.

Munson, P.J., et al., "LIGAND: A versatile computerized approach for characterization of ligand-binding systems," *Anal. Biochem.*, 1980, 107, 220-239.

Nemeroff, C.B., et al., "Reduced corticotrophin releasing factor binding sites in the frontal cortex of suicide victims," *Arch. Gen. Psychiatry*, Jun. 1988, 45, 577-579.

Nemeroff, C.B., et al., "Elevated concentrations of CSF corticotrophin-releasing factor-like immunoreactivity in depressed patients," *Science*, 1984, 226, 1342-1344.

Newport, D.J., et al., Neurobiology of posttraumatic stress disorder, *Curr. Opin. Neurobiology*, 2000, 10, 211-218.

Owens, M.J., et al., "Corticotropin-releasing factor antagonists in affective disorders," *Expert Opin. Invest. Drugs*, 1999, 8(11), 1849-1858.

Remington's Pharmaceutical Sciences, 17th Ed., *Mack Publishing Company, Easton, PA.*, 1985.

Rivier, J., et al., "Characterization of rat hypothalamic corticotrophin-releasing factor," *Proc. Nat. Acad. Sci. (USA)*, Aug. 1983, 80, 4851-4855.

Sapolsky, R.M., "Hypercortisolism among socially subordinate wild baboons originates at the CNS level," *Arch. Gen. Psychiatry*, 1989, 46, 1047-1051.

Swerdlow, N.R., et al., "Corticotropin-releasing factor potentiates acoustic startle in rats: blockade by chlordiazepoxide," *Psychopharmacology*, 1986, 88, 147-152.

Vale, W., et al., Chemical and biological characterization of corticotrophin releasing factor, *Rec. Prog. Horm. Res.*, 1983, 39 245-271.

Vale, W., et al., "characterization of a 41-residue ovine hypothalamic peptide that stimulates secretion of corticotrophin and β-endorphin," *Science*, 1981, 213, 1394-1397.

Webster, E., et al., "Corticotropin-releasing hormone and inflammation," *Ann. N.Y. Acad. Sci.*, 1998, 840, 21-32.

3,7-DIHYDRO-PURINE-2,6-DIONE DERIVATIVES AS CRF RECEPTOR LIGANDS

CROSS-REFERENCE TO RELATED APPLICATIONS

This application is a divisional of U.S. application Ser. No. 10/289,851, filed Nov. 7, 2002 now abandoned, which in turn claims priority of U.S. Provisional Appl No. 60/331,829, filed Nov. 20, 2001. The disclosure of each of these prior applications is incorporated herein by reference in its entirety.

FIELD OF THE INVENTION

This invention relates to 3,7-dihydro-purine-2,6-dione derivatives as CRF antagonists, pharmaceutical compositions containing the same, and methods of using the same in the treatment of psychiatric disorders and neurological diseases including affective disorder, anxiety related disorders, depression, headache, post-traumatic stress disorder, supranuclear palsy, Alzheimer's disease, head and spinal cord traumas, anorexia nervosa or other feeding disorders, as well as treatment of irritable bowel syndrome, gastrointestinal diseases, cardiovascular or heart-related diseases, immune supression, human immunodeficiency virus infections, fertility problems, or a disorder the treatment of which can be effected or facilitated by antagonizing CRF, including but not limited to disorders induced or facilitated by CRF.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebrospinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)). Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome post-operative ileus and colonic hypersensitivity associated with psychopathological disturbance and stress [for reviews see E. D. DeSouza, C. B. Nemeroff, Editors; Corticotropin-Releasing Factor: Basic and *Clinical Studies of a Neuropeptide*, E. B. De Souza and C. B. Nemeroff eds., CRC Press p221 (1990) and C. Maillot, M. Million, J. Y. Wei, A. Gauthier, Y. Tache, Gastroenterology, 119, 1569–1579 (2000)].

Over-expression or under-expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress [for reviews see J. R. McCarthy, S. C. Heinrichs and D. E. Grigoriadis, Cuur. Pharm. Res., 5, 289–315 (1999); P. J. Gilligan, D. W. Robertson and R. Zaczek, J. Medicinal Chem., 43, 1641–1660 (2000), G. P. Chrousos, Int. J. Obesity, 24, Suppl. 2, S50–S55 (2000); E. Webster, D. J. Torpy, I. J. Elenkov, G. P. Chrousos, Ann. N.Y. Acad. Sci., 840, 21–32 (1998); D. J. Newport and C. B. Nemeroff, Curr. Opin. Neurobiology, 10, 211–218 (2000); G. Mastorakos and I. Ilias, Ann. N.Y. Acad. Sci., 900, 95–106 (2000); M. J. Owens and C. B. Nemeroff, Expert Opin. Invest. Drugs, 8, 1849–1858 (1999); G. F. Koob, Ann. N.Y. Acad. Sci., 909, 170–185 (2000)].

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and, WO00/01675.

SUMMARY OF THE INVENTION

This invention relates to a method of treating a mammal afflicted with a disorder selected from affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia, which method comprises administering to the mammal a therapeutically effective amount of a compound of formula (I):

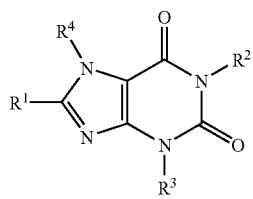

or a pharmaceutically acceptable salt form thereof, wherein:

$R^1$ is selected from the group consisting of H, $C_{1-4}$ alkyl, $C_{3-8}$ cycloalkyl, $C_{2-4}$ alkenyl and $C_{2-4}$ alkynyl, wherein each is optionally substituted with 0–3 substituents independently selected from the group consisting of —CN, hydroxy, halo and $C_{1-4}$ alkoxy;

alternatively $R^1$ is selected from the group consisting of —CN, —CF$_3$, —C$_2$F$_5$, H, $C_1$–$C_6$ alkyl-NR$^{1a}$R$^{1b}$, —NR$^{1a}$C(O)R$^{1b}$, —C(O)NR$^{1a}$R$^{1b}$, —OR$^{1a}$, S(O)$_n$R$^{1a}$ and —OC(O)R$^{1a}$, wherein R$^{1a}$ and R$^{1b}$ are independently selected from the group consisting of H, $C_1$–$C_4$ alkyl and $C_3$–$C_6$ cycloalkyl, and wherein R$^{1a}$ and R$^{1b}$ are each optionally substituted with 0–3 substituents independently selected from the group consisting of —CN, hydroxy, halo and $C_{1-4}$ alkoxy;

n is 0, 1 or 2;

$R^2$ is selected from the group consisting of H, $C_1$–$C_6$ alkyl, $C_3$–$C_7$ cycloalkyl, $C_3$–$C_6$-cycloalkyl-$C_1$–$C_6$ alkyl, $C_3$–$C_6$-alkenyl, $C_3$–$C_6$-alkynyl, aryl, heteroaryl and $C_5$–$C_8$ cycloalkenyl, wherein each is optionally substituted with 0 to 4 substituents independently selected at each occurrence from the group consisting of halogen, —OH, $C_2$–$C_4$ alkenyl, $C_2$–$C_4$ alkynyl, $C_2$–$C_4$ cycloalkyl, $C_1$–$C_4$ haloalkyl, —CO$_2$R$^5$ —OC(O)R$^5$, —COR$^5$, —OC(O)OR$^5$, —CO$_2$H, —OR$^5$, —NR$^6$R$^7$, —NR$^5$COR$^7$, —NHR$^5$SO$_2$R$^7$, —OC(O)NR$^5$R$^6$, —N(COR$^5$)$_2$, —NR$^5$CONR$^6$R$^7$, —NR$^5$CO$_2$R$^7$, —CONR$^5$R$^7$, —S(O)$_n$R$^5$, —SO$_2$NR$^5$R$^7$, —SH, —CN, aryl, heteroaryl and heterocyclyl;

$R^3$ is selected from the group consisting of aryl and heteroaryl;

$R^4$ is selected from the group consisting of $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, aryl, heteroaryl, heterocyclyl and benzyl;

$R^4$ is optionally substituted with 0–1 substituents selected from the group consisting of —CN, —S(O)$_n$R$^9$, —COR$^{10}$, —CO$_2$R$^{10}$, —NR$^{11}$COR$^{10}$, —N(COR$^{10}$)$_2$, —NR$^{11}$CONR$^{10}$R$^{12}$, —NR$^{11}$CO$_2$R$^9$, —CONR$^{10}$R$^{12}$, 1-naphthalenyl, 1-morpholinyl, 1-piperidinyl, 1-piperazinyl and $C_{3-8}$ cycloalkyl, wherein 0–1 carbon atoms in the $C_{3-8}$ cycloalkyl is replaced by a group selected from the group consisting of —S(O)$_n$—, —NR$^{10}$—, —NCO$_2$R$^9$—, —NCOR$^9$— and —NSO$_2$R$^9$—, and wherein N$^4$ in 1-piperazinyl is optionally substituted with 0–1 substituents selected from the group consisting of R$^{10}$, CO$_2$R$^9$, COR$^9$ and SO$_2$R$^9$;

alternatively $R^4$ is optionally substituted with 0–3 substituents independently selected at each occurrence from the group consisting of aryl, heteroaryl, heterocyclyl, $C_{1-6}$ alkyl, $C_{2-8}$ alkenyl, $C_{2-8}$ alkynyl, Br, Cl, F, I, $C_{1-4}$ haloalkyl, —OR$^{10}$, —NR$^{10}$R$^{12}$, $C_{1-4}$ alkoxy-$C_{1-4}$ alkyl and $C_{3-8}$ cycloalkyl which is optionally substituted with 0–1 R$^8$ and wherein 0–1 carbon atoms in the $C_{3-8}$ cycloalkyl is replaced by —O—;

$R^5$ is selected from the group consisting of H, $C_1$–$C_4$ alkyl, $C_3$–$C_6$ cycloalkyl, $C_3$–$C_4$ alkenyl, $C_3$–$C_4$ alkynyl, $C_1$–$C_4$ haloalkyl, $C_1$–$C_4$ alkyloxy-$C_1$–$C_4$ alkyl and $C_3$–$C_6$ cycloalkyl-$C_1$–$C_4$ alkyl, wherein one carbon atom in any cycloalkyl ring may be replaced with O, S or NR$^6$, and wherein $C_1$–$C_4$ alkyl, $C_3$–$C_6$ cycloalkyl, $C_3$–$C_4$ alkenyl, $C_3$–$C_4$ alkynyl, $C_1$–$C_4$ haloalkyl, $C_1$–$C_4$ alkyloxy-$C_1$–$C_4$ alkyl and $C_3$–$C_6$ cycloalkyl-$C_1$–$C_4$ alkyl are each optionally substituted with 0 to 2 substituents independently selected at each occurrence from the group consisting of —OH, $C_1$–$C_4$ alkoxy and halogen;

$R^6$ is selected from the group consisting of H, $C_1$–$C_4$ alkyl, $C_3$–$C_6$ cycloalkyl, $C_3$–$C_6$ cycloalkyl-$C_1$–$C_4$ alkyl and $C_1$–$C_4$ haloalkyl;

$R^7$ is selected from the group consisting of H, $C_1$–$C_4$ alkyl, $C_3$–$C_6$ cycloalkyl, $C_3$–$C_4$ alkenyl, $C_3$–$C_4$ alkynyl, $C_1$–$C_4$ haloalkyl, aryl, $C_1$–$C_4$ alkyloxy-$C_1$–$C_4$ alkyl and $C_3$–$C_6$ cycloalkyl-$C_1$–$C_4$ alkyl, wherein one carbon in any cycloalkyl ring may be replaced with O, S or $NR^6$, and wherein $C_1$–$C_4$ alkyl, $C_3$–$C_6$ cycloalkyl, $C_3$–$C_4$ alkenyl, $C_3$–$C_4$ alkynyl, $C_1$–$C_4$ haloalkyl, aryl, $C_1$–$C_4$ alkyloxy-$C_1$–$C_4$ alkyl and $C_3$–$C_6$ cycloalkyl-$C_1$–$C_4$ alkyl are each optionally substituted with 0 to 2 substituents independently selected at each occurrence from the group consisting of $C_1$–$C_4$ alkoxy and halogen;

$R^8$ is selected from the group consisting of H, $C_{1-4}$ alkyl, $C_{3-6}$ cycloalkyl-$C_{1-4}$ alkyl and $C_{3-8}$ cycloalkyl;

$R^9$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl and $C_{3-6}$ cycloalkyl-$C_{1-6}$ alkyl;

$R^{10}$ is selected from the group consisting of H, benzyl, aryl, $C_{1-4}$ alkyl, $C_{1-4}$ haloalkyl, $C_{1-4}$ alkoxy-$C_{1-4}$ alkyl, $C_{3-6}$ cycloalkyl and $C_{3-6}$ cycloalkyl-$C_{1-6}$ alkyl;

$R^{11}$ is selected from the group consisting of H, $C_{1-4}$ alkyl, $C_{3-7}$ cycloalkyl and $C_{3-6}$ cycloalkyl-$C_{1-6}$ alkyl;

$R^{12}$ is selected from the group consisting of H, $C_{1-4}$ alkyl, $C_{1-4}$ haloalkyl, $C_{1-4}$ alkoxy-$C_{1-4}$ alkyl, $C_{3-6}$ cycloalkyl and $C_{3-6}$ cycloalkyl-$C_{1-6}$ alkyl;

$R^{13}$ is selected from the group consisting of H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-4}$ alkyl, $C_{1-4}$ haloalkyl, $R^{16}S(O)_n$—$C_{1-4}$ alkyl and $R^9R^{10}N$—$C_{2-4}$ alkyl;

$R^{14}$ and $R^{15}$ are independently selected at each occurrence from the group consisting of H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl and $C_{1-4}$ haloalkyl;

alternatively, in an —$NR^{13}R^{14}$ moiety, $R^{13}$ and $R^{15}$ taken together form 1-pyrrolidinyl, 1-morpholinyl, 1-piperidinyl or 1-piperazinyl, wherein $N^4$ in 1-piperazinyl is optionally substituted with 0–1 substituents selected from the group consisting of $R^{17}$, $CO_2R^{16}$, $COR^{16}$ and $SO_2R^{16}$;

$R^{16}$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl, heteroaryl($C_{1-4}$ alkyl)- and benzyl, wherein each benzyl being optionally substituted on the aryl moiety with 0–1 substituents selected from the group consisting of $C_{1-4}$ alkyl, Br, Cl, F, I, $C_{1-4}$ haloalkyl, nitro, $C_{1-4}$ alkoxy $C_{1-4}$ haloalkoxy and dimethylamino;

$R^{17}$ is selected from the group consisting of H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl($C_{1-4}$ alkyl)-;

$R^{18}$ is selected from the group consisting of H, $C_{1-4}$ alkyl, $C_{3-7}$ cycloalkyl, $C_{3-6}$ cycloalkyl-$C_{1-6}$ alkyl, phenyl and benzyl, each phenyl or benzyl being optionally substituted on the aryl moiety with 0–3 groups chosen from the group consisting of $C_{1-4}$ alkyl, Br, Cl, F, I, $C_{1-4}$ haloalkyl, nitro, $C_{1-4}$ alkoxy, $C_{1-4}$ haloalkoxy and dimethylamino;

$R^{19}$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being optionally substituted on the aryl moiety with 0–1 substituents selected from the group consisting of $C_{1-4}$ alkyl, Br, Cl, F, I, $C_{1-4}$ haloalkyl, nitro, $C_{1-4}$ alkoxy, $C_{1-4}$ haloalkyl and dimethylamino;

aryl is selected from the group consisting of phenyl, naphthyl, indanyl and indenyl, each aryl optionally substituted with 0–5 substituents independently selected at each occurrence from the group consisting of phenyl, $C_{1-6}$ alkyl, $C_{3-6}$ cycloalkyl, methylenedioxy, $C_{1-4}$ alkoxy-$C_{1-4}$ alkoxy, —$OR^{13}$, Br, Cl, F, I, $C_{1-4}$ haloalkyl, —CN, —$NO_2$, SH, —$S(O)_nR^{14}$, —$COR^{13}$, —$CO_2R^{13}$, —$OC(O)R^{14}$, —$NR^{18}COR^{13}$, —$N(COR^{13})_2$, —$NR^{18}CONR^{13}R^{15}$, —$NR^{18}CO_2R^{14}$, —$NR^{13}R^{15}$ and —$CONR^{13}R^{15}$;

heteroaryl is selected from the group consisting of pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being optionally substituted with 0–4 substituents independently selected at each occurrence from the group consisting of $C_{1-6}$ alkyl, $C_{3-6}$ cycloalkyl, Br, Cl, F, I, $C_{1-4}$ haloalkyl, —CN, nitro, —$OR^{13}$, SH, —$S(O)_nR^{14}$, —$COR^{13}$, —$CO_2R^{13}$, —$OC(O)R^{14}$, —$NR^{18}COR^{13}$, —$N(COR^{13})_2$, —$NR^{18}CONR^{13}R^{15}$, —$NR^{18}CO_2R^{14}$, —$NR^{13}R^{15}$ and —$CONR^{13}R^{15}$, and wherein each heteroaryl is optionally substituted on any nitrogen atom with 0–1 substituents selected from the group consisting of $R^{18}$, $CO_2R^{19}$, $COR^{19}$ and $SO_2R^{19}$; and heterocyclyl is saturated or partially saturated heteroaryl, morpholinyl, thiomorpholinyl, piperazinyl, each optionally substituted with 1–3 substituents independently selected at each occurrence from the group consisting of $C_1$–$C_6$ alkyl, $C_3$–$C_6$ cycloalkyl, $C_2$–$C_6$ alkenyl, $C_2$–$C_6$ alkynyl, halogen, $C_1$–$C_4$ haloalkyl, —CN, —$OR^5$, —SH, —$NO_2$, —$OCF_3$, —$S(O)_nR^5$, —$COR^5$, —$CO_2R^5$, —$OC(O)R^5$, —$NR^5COR^6$, —$N(COR^5)_2$, —$NR^5CONR^5R^6$, —$NR^5CO_2R^6$, —$NR^5R^6$ and —$CONR^5R^6$.

In further embodiments, the methods of the present invention encompass compounds of Formula (I) wherein:

$R^1$ is selected from the group consisting of $C_{1-4}$ alkyl, $C_{3-8}$ cycloalkyl, $C_{2-4}$ alkenyl and $C_{2-4}$ alkynyl, wherein each is optionally substituted with 0–3 substituents independently selected from the group consisting of —CN, hydroxy, halo and $C_{1-4}$ alkoxy;

$R^2$ is selected from the group consisting of $C_1$–$C_6$ alkyl, $C_3$–$C_7$ cycloalkyl, $C_3$–$C_6$-alkenyl, and $C_3$–$C_6$-alkynyl, wherein each is optionally substituted with 0 to 4 substituents independently selected at each occurrence from the group consisting of halogen, —OH, $C_2$–$C_4$ alkenyl, $C_2$–$C_4$ alkynyl, $C_2$–$C_4$ cycloalkyl, $C_1$–$C_4$ haloalkyl, —$CO_2R^5$—$OC(O)R^5$, —$COR^5$, —$OC(O)OR^5$, —$CO_2H$, —$OR^5$, —$NR^6R^7$, —$NR^5COR^7$, —$NHR^5SO_2R^7$, —$OC(O)NR^5R^6$, —$N(COR^5)_2$, —$NR^5CONR^6R^7$, —$NR^5CO_2R^7$, —$CONR^5R^7$, —$S(O)_nR^5$, —$SO_2NR^5R^7$, —SH, and —CN;

$R^3$ is phenyl optionally substituted with 0–5 substituents independently selected at each occurrence from the group consisting of phenyl, $C_{1-6}$ alkyl, $C_{3-6}$ cycloalkyl, methylenedioxy, $C_{1-4}$ alkoxy-$C_{1-4}$ alkoxy, —$OR^{13}$, Br, Cl, F, I, $C_{1-4}$ haloalkyl, —CN, —$NO_2$, SH, —$S(O)_nR^{14}$, —$COR^{13}$, —$CO_2R^{13}$, —$OC(O)R^{14}$, —$NR^{18}COR^{13}$, —$N(COR^{13})_2$, —$NR^{18}CONR^{13}R^{15}$, —$NR^{18}CO_2R^{14}$, —$NR^{13}R^{15}$ and —$CONR^{13}R^{15}$, or pyridyl optionally substituted with 0–4 substituents independently selected at each occurrence from the group consisting of $C_{1-6}$ alkyl, $C_{3-6}$ cycloalkyl, Br, Cl, F, I, $C_{1-4}$ haloalkyl, —CN, nitro, —$OR^{13}$, SH, —$S(O)_nR^{14}$, —$COR^{13}$, —$CO_2R^{13}$, —OC(O)R$^{14}$, —NR$^{18}$COR$^{13}$, —N(COR$^{13}$)$_2$, —NR$^{18}$CONR$^{13}$R$^{15}$, —NR$^{18}$CO$_2$R$^{14}$, —NR$^{13}$R$^{15}$ and —CONR$^{13}$R$^{15}$; and R$^4$ is selected from the group consisting of C$_{1-10}$ alkyl, C$_{2-10}$ alkenyl, C$_{2-10}$ alkynyl, C$_{3-8}$ cycloalkyl, and benzyl;

R$^4$ is optionally substituted with 0–1 substituents selected from the group consisting of —CN, —S(O)$_n$R$^9$, —COR$^{10}$, and 1-naphthalenyl;

alternatively R$^4$ is optionally substituted with 0–3 substituents independently selected at each occurrence from the group consisting of aryl, C$_{1-6}$ alkyl, C$_{2-8}$ alkenyl, —OR$^{10}$, —NR$^{10}$R$^{12}$, CF$_3$, C$_{1-4}$ alkoxy-C$_{1-4}$ alkyl and C$_{3-8}$ cycloalkyl which is optionally substituted with 0–1 R$^8$ and wherein 0–1 carbon atoms in the C$_{3-8}$ cycloalkyl is replaced by —O—.

In even further embodiments, the methods of the present invention encompass compounds of Formula (I) wherein:

R$^1$ is selected from the group consisting of C$_{1-4}$ alkyl, —CF$_3$, —C$_2$F$_5$, CN, and OR$^{1a}$;

R$^{1a}$ is selected from the group consisting of C$_{1-4}$ alkyl substituted with 0–3 halo;

R$^2$ is selected from the group consisting of C$_1$–C$_6$ alkyl and C$_3$–C$_7$ cycloalkyl, each optionally substituted with 0 to 4 substituents independently selected at each occurrence from the group consisting of halogen, —OH, C$_2$–C$_4$ alkenyl, C$_2$–C$_4$ alkynyl, C$_2$–C$_4$ cycloalkyl, C$_1$–C$_4$ haloalkyl, —CO$_2$R$^5$ —OC(O)R$^5$, —COR$^5$, —OC(O)OR$^5$, —CO$_2$H, —OR$^5$, —NR$^6$R$^7$, —NR$^5$COR$^7$, —NHR$^5$SO$_2$R$^7$, —OC(O)NR$^5$R$^6$, —N(COR$^5$)$_2$, —NR$^5$CONR$^6$R$^7$, —NR$^5$CO$_2$R$^7$, —CONR$^5$R$^7$, —S(O)$_n$R$^5$, —SO$_2$NR$^5$R$^7$, —SH, and —CN;

R$^3$ is phenyl optionally substituted with 0–5 substituents independently selected at each occurrence from the group consisting of phenyl, C$_{1-6}$ alkyl, C$_{3-6}$ cycloalkyl, methylenedioxy, C$_{1-4}$ alkoxy-C$_{1-4}$ alkoxy, —OR$^{13}$, Br, Cl, F, I, C$_{1-4}$ haloalkyl, —CN, —NO$_2$, SH, —S(O)$_n$R$^{14}$, —COR$^{13}$, —CO$_2$R$^{13}$, —OC(O)R$^{14}$, —NR$^{18}$COR$^{13}$, —N(COR$^{13}$)$_2$, —NR$^{18}$CONR$^{13}$R$^{15}$, —NR$^{18}$CO$_2$R$^{14}$, —NR$^{13}$R$^{15}$ and —CONR$^{13}$R$^{15}$, or pyridyl substituted with 0–4 substituents independently selected at each occurrence from the group consisting of C$_{1-6}$ alkyl, C$_{3-6}$ cycloalkyl, Br, Cl, F, I, C$_{1-4}$ haloalkyl, —CN, nitro, —OR$^{13}$, SH, —S(O)$_n$R$^{14}$, —COR$^{13}$, —CO$_2$R$^{13}$, —OC(O)R$^{14}$, —NR$^{18}$COR$^{13}$, —N(COR$^{13}$)$_2$, —NR$^{18}$CONR$^{13}$R$^{15}$, —NR$^{18}$CO$_2$R$^{14}$, —NR$^{13}$R$^{15}$ and —CONR$^{13}$R$^{15}$; and R$^4$ is selected from the group consisting of C$_{1-10}$ alkyl, C$_{2-10}$ alkenyl, C$_{2-10}$ alkynyl, C$_{3-8}$ cycloalkyl, and benzyl;

R$^4$ is optionally substituted with 0–1 substituents selected from the group consisting of —CN, —S(O)$_n$R$^9$, —COR$^{10}$, and 1-naphthalenyl;

alternatively R$^4$ is optionally substituted with 0–3 substituents independently selected at each occurrence from the group consisting of aryl, C$_{1-6}$ alkyl, C$_{2-8}$ alkenyl, —OR$^{10}$, —NR$^{10}$R$^{12}$, CF$_3$, C$_{1-4}$ alkoxy-C$_{1-4}$ alkyl and C$_{3-8}$ cycloalkyl which is optionally substituted with 0–1 R$^8$ and wherein 0–1 carbon atoms in the C$_{3-8}$ cycloalkyl is replaced by —O—.

Embodiments of this invention further include compounds of Formula (I) or pharmaceutically acceptable salts or pro-drug forms thereof as CRF receptor ligands, wherein:

R$^1$ is selected from the group consisting of C$_{1-4}$ alkyl, CN, and CF$_3$;

alternatively R$^1$ is —OR$^{1a}$, wherein R$^{1a}$ is C$_1$–C$_4$ alkyl;

n is 0, 1 or 2;

R$^2$ is selected from the group consisting of C$_1$–C$_6$ alkyl and C$_3$–C$_7$ cycloalkyl;

R$^3$ is selected from the group consisting of aryl and heteroaryl;

R$^4$ is selected from the group consisting of C$_{1-10}$ alkyl, C$_{3-8}$ cycloalkyl and benzyl;

R$^4$ is optionally substituted with 0–1 1-naphthalenyl groups;

alternatively R$^4$ is optionally substituted with 0–3 substituents independently selected at each occurrence from the group consisting of aryl, C$_{1-6}$ alkyl, C$_{2-8}$ alkenyl, —OR$^{10}$, —NR$^{10}$R$^{12}$, CF$_3$, C$_{1-4}$ alkoxy-C$_{1-4}$ alkyl and C$_{3-8}$ cycloalkyl;

R$^{10}$ is selected from the group consisting of H and benzyl;

R$^{13}$ is selected from the group consisting of C$_{1-6}$ alkyl and C$_{1-4}$ haloalkyl;

aryl is phenyl optionally substituted with 0–5 substituents independently selected at each occurrence from the group consisting of phenyl, C$_{1-6}$ alkyl, —OR$^{13}$, Br, Cl, F, I and C$_{1-4}$ haloalkyl; and heteroaryl is pyridyl optionally substituted with 0–4 substituents independently selected at each occurrence from the group consisting of C$_{1-6}$ alkyl and —OR$^{13}$.

Another embodiment of this invention includes compounds of Formula (I) and pharmaceutically acceptable salts and pro-drug forms thereof as CRF receptor ligands which are selected from the group consisting of:

3-(2,4-dichlorophenyl)-8-ethyl-1-methyl-7-(3-pentyl)-3,7-dihydro-1H-purine-2,6-dione 3-(2,4-dichlorophenyl)-8-ethyl-7-(4-heptyl)-1-methyl-3,7-dihydro-1H-purine-2,6-dione 7-benzyloxymethyl-3-(2,4-dichlorophenyl)-8-ethyl-1-methyl-3,7-dihydro-1H-purine-2,6-dione 7-(1-allyl-3-butenyl)-3-(2,4-dichlorophenyl)-8-ethyl-1-methyl-3,7-dihydro-1H-purine-2,6-dione 3-(2,4-dichlorophenyl)-1-methyl-7-(3-pentyl)-3,7-dihydro-1H-purine-2,6-dione 3-(2,4-dichlorophenyl)-7-(4-heptyl)-1-methyl-3,7-dihydro-1H-purine-2,6-dione 3-(2,4-dichlorophenyl)-8-ethyl-7-(4-methoxybenzyl)-1-methyl-3,7-dihydro-1H-purine-2,6-dione 3-[2-chloro-4-(isopropylphenyl)]-8-ethyl-1-methyl-7-(3-pentyl)-3,7-dihydro-1H-purine-2,6-dione 3-[2-chloro-4-(isopropylphenyl)]-8-ethyl-7-(4-heptyl)-1-methyl-3,7-dihydro-1H-purine-2,6-dione 3-[2-chloro-4-(isopropylphenyl)]-1-methyl-7-(3-pentyl)-3,7-dihydro-1H-purine-2,6-dione 3-[2-chloro-4-(isopropylphenyl)]-7-(4-heptyl)-1-methyl-3,7-dihydro-1H-purine-2,6-dione 8-ethyl-7-(4-heptyl)-1-methyl-3-(2,4,6-trimethylphenyl)-3,7-dihydro-1H-purine-2,6-dione 8-ethyl-7-(4-heptyl)-3-(4-methoxy-2-methylpyrid-3-yl)-1-methyl-3,7-dihydro-1H-purine-2,6-dione Also provided herein is a pharmaceutical composition comprising one or more compounds of Formula (I) and a pharmaceutically acceptable carrier.

DETAILED DESCRIPTION OF THE INVENTION

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms or a structure are intended, unless the specific stereochemistry or isomer form is specifically indicated.

The term "alkyl" as used herein is directed to a saturated hydrocarbon group (designated by the formula $C_nH2_{n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., *Hawley's Condensed Chemical Dictionary* (13 ed.), R. J. Lewis, ed., J. Wiley & Sons, Inc., New York (1997)). Aryl groups include, without limitation, phenyl, naphthyl, indanyl and indenyl.

"Heteroaryl" rings are aryl rings in which one or more, typically from 1–4, of the ring-member carbon atoms is replaced by an atom other than a carbon atom, i.e., a heteroatom (typically O, N or S). Heteroaryl includes, without limitation: pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane. Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen on the designated atom is replaced with a selection from the indicated group, provided that the designated atom's normal valency is not exceeded, and that the substitution results in a stable compound.

"Unsubstituted" atoms bear all of the hydrogen atoms dictated by their valency. When a substituent is keto, then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the compounds of Formula (I), and the like.

The term "therapeutically effective amount" of a compound of this invention means an amount effective to antagonize abnormal level of CRF or treat the symptoms of affective disorder, anxiety or depression in a host.

The compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety herein by reference.

The compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 1 are prepared by the method outlined in Scheme 1. An appropriately substituted aryl or heteroaryl isocyanate (2) is treated with a primary alkylamine in a suitable solvent, such as THF, to form ureas of formula 3. The ureas of formula 3 are dissolved in acetic anhydride and treated with cyanoactic acid. Subsequent treatment with a base such as aqueous NaOH results in the formation of uricils of formula 4. Nitrosation of intermediate 4 with a reagent, such as $NaNO_2$, and subsequent reduction with a suitable reagent, such as $Na_2S_2O_4$, affords the corrosponding diamines (6). Appropriate cyclization conditions, such as the use of orthoesters, yields compounds of formula 7. Compounds of formula 1 can be derived from compounds of formula 7 by treatment of 7 with a suitable base such as, but not limited to, NaH, KH, $K_2CO_3$, $Na_2CO_3$, i-$Pr_2$NEt, NaOMe, NaOEt and $Et_3$N and a suitable alkylating agent $R_4X$ such as, but not limited to, alkyl halides, tosylates, mesylates and triflates in a suitable inert solvent such as, but not limited to, DMF, THF, $CH_2Cl_2$, dioxane, toluene and DMSO. Compounds of formula 1 can also be derived from compounds of formula 7 by treatment of 7 with an alcohol $R_4$OH, a phosphine $PR^a_3$ (where $R^a$ is lower alkyl, phenyl or substituted phenyl or furyl) and an azodicarboxylate ester $R^bO_2CN=NCO_2R^b$ (where $R^b$ is lower alkyl) in an inert solvent at temperatures ranging from 0° C. to 150° C. Inert solvent may include but is not limited to polyethers (preferably 1,2-dimethoxyethane), dialkyl ethers (preferably diethylether), cyclic ethers (preferably tetrahydrofuran or 1,4-dioxane) or aromatic hydrocarbons (preferably benzene or toluene). The choices of phosphine, solvent or azodicarboxylate ester are known to those skilled in the art of organic chemistry as described by Mitsunobu (Mitsunobu, O. *Synthesis* 1981, 1).

SCHEME 1

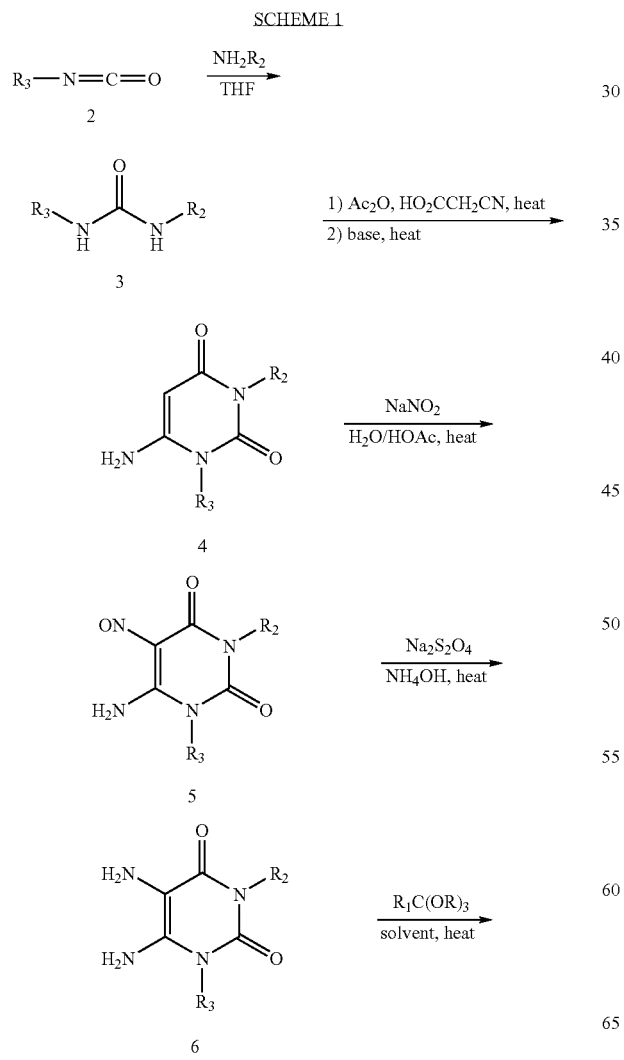

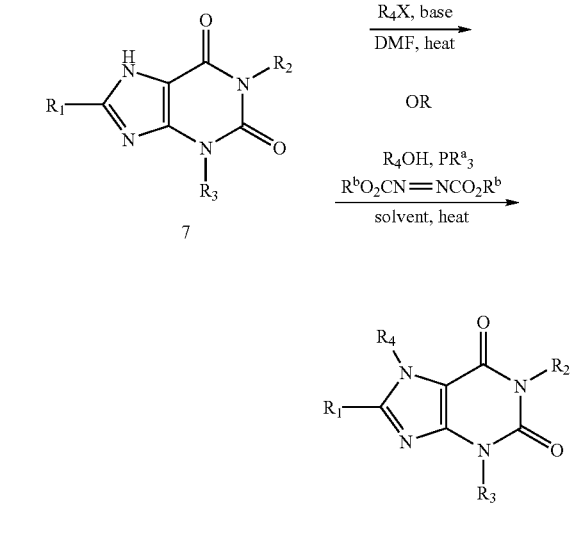

For some of the examples, the aryl or heteroaryl $R_3$ substituent can be functionalized further by treatment with reagents known to one skilled in the art of organic synthesis (for example, N-bromosuccinimide, bromine, N-chlorosuccinimide, alkyl halides, acid chlorides, etc., preferably N-chlorosuccinimide) (Scheme 2).

SCHEME 2

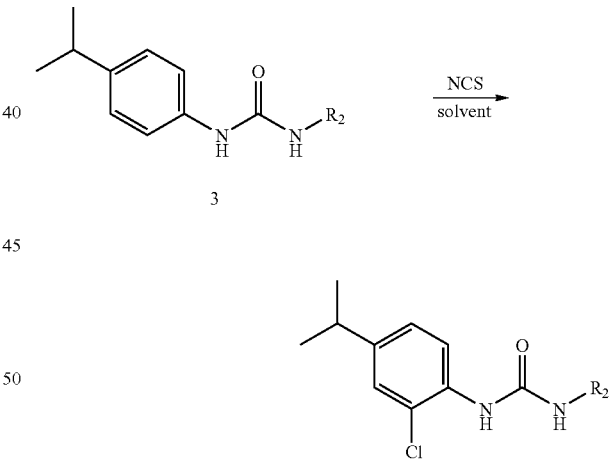

Compounds of formula 1 are also prepared by the method outlined in Scheme 3. Compound 8 is prepared using the route outlined in Scheme 1 where P is a protecting group which can be removed using conditions under which the other functional groups of the compound are stable. The protecting group, preferably p-methoxybenzyl, is removed using conditions described in *Protective Groups in Organic Synthesis* (Greene, Wuts; 3$^{rd}$ ed., 1999, John Wiley & Sons, Inc.), preferably by heating in trifluoroacetic acid at temperatures ranging from 25° C. to 150° C. to provide 9. If the reaction temperature exceeds the boiling point of trifluoroacetic acid, the reaction must be carried out in a pressure tube. Compound 9 is coupled with aryl or heteroarylboronic acids using conditions described by Lam et. al. (Lam, P. Y. S.; Clark, C. G.; Saubern, S.; Adams, J.; Averill, K. M.; Chan, D. M. T.; Combs, A. *Synlett*. 2000, 5, 674.) to form compound 1.

SCHEME 3

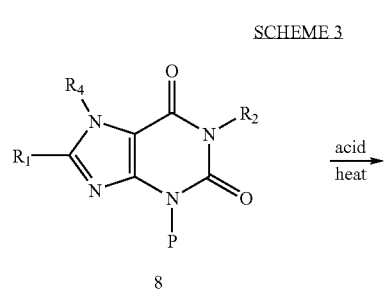

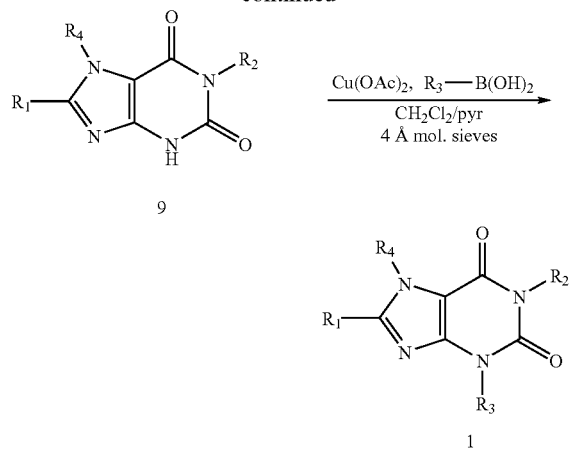

Various analogs synthesized using Schemes 1–3 are listed in Table 1.

TABLE 1

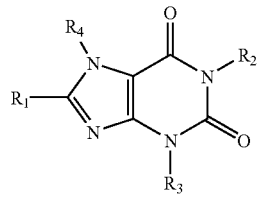

| Ex | R$_1$ | R$_2$ | R$_3$ | R$_4$ | (M + H)$^+$ | Mp (° C.) |
|---|---|---|---|---|---|---|
| 1 | Et | Me | 2,4-Cl$_2$—Ph | 3-pentyl | 409.1212 | 186–187 |
| 2 | Et | Me | 2,4-Cl$_2$—Ph | 4-heptyl | 437.1532 | 185–186 |
| 3 | Et | Me | 2,4-Cl$_2$—Ph | benzyloxymethyl | 459.1011 | amorph solid |
| 4 | Et | Me | 2,4-Cl$_2$—Ph | CH(CH$_2$CH=CH$_2$)$_2$ | 433.1202 | 145–146 |
| 5 | H | Me | 2,4-Cl$_2$—Ph | 3-pentyl | 381.0889 | 158–159 |
| 6 | H | Me | 2,4-Cl$_2$—Ph | 4-heptyl | 409.1192 | amorph solid |
| 7 | Et | Me | 2,4-Cl$_2$—Ph | 4-methoxybenzyl | 459.0975 | 209–210 |
| 8 | Et | Me | 2,4-Cl$_2$—Ph | 1-cyclopropylethyl | | |
| 9 | Et | Me | 2,4-Cl$_2$—Ph | 1-cyclopropylpropyl | | |
| 10 | Et | Me | 2,4-Cl$_2$—Ph | 1-cyclopropylbutyl | | |
| 11 | Et | Me | 2,4-Cl$_2$—Ph | 1-cyclopropyl-2-methoxyethyl | | |
| 12 | Et | Me | 2,4-Cl$_2$—Ph | 1-cyclobutylethyl | | |
| 13 | Et | Me | 2,4-Cl$_2$—Ph | 1-cyclobutylpropyl | | |
| 14 | Et | Me | 2,4-Cl$_2$—Ph | 1-cyclobutylbutyl | | |
| 15 | Et | Me | 2,4-Cl$_2$—Ph | 1-cyclobutyl-2-methoxyethyl | | |
| 16 | Et | Me | 2,4-Cl$_2$—Ph | dicyclobutylmethyl | | |
| 17 | Et | Me | 2,4-Cl$_2$—Ph | CH(CH$_2$OMe)$_2$ | | |
| 18 | Et | Me | 2,4-Cl$_2$—Ph | CH(i-Pr)Et | | |
| 19 | Et | Me | 2,4-Cl$_2$—Ph | CH(i-Pr)Pr | | |
| 20 | Et | Me | 2,4-Cl$_2$—Ph | CH(i-Pr)CH$_2$OMe | | |
| 21 | OMe | Me | 2,4-Cl$_2$—Ph | 3-pentyl | | |
| 22 | OMe | Me | 2,4-Cl$_2$—Ph | 4-heptyl | | |
| 23 | Et | Et | 2,4-Cl$_2$—Ph | 3-pentyl | | |
| 24 | Et | Et | 2,4-Cl$_2$—Ph | 4-heptyl | | |
| 25 | Et | Et | 2,4-Cl$_2$—Ph | CH(CH$_2$OMe)Pr | | |
| 26 | Et | Pr | 2,4-Cl$_2$—Ph | 3-pentyl | | |
| 27 | Et | Pr | 2,4-Cl$_2$—Ph | 4-heptyl | | |
| 28 | Et | Pr | 2,4-Cl$_2$—Ph | CH(CH$_2$OMe)Pr | | |
| 29 | Et | c-Pr | 2,4-Cl$_2$—Ph | 3-pentyl | | |
| 30 | Et | c-Pr | 2,4-Cl$_2$—Ph | 4-heptyl | | |
| 31 | Et | c-Pr | 2,4-Cl$_2$—Ph | CH(CH$_2$OMe)Pr | | |
| 32 | OMe | Me | 2,4-Cl$_2$—Ph | CH(CH$_2$OMe)Pr | | |
| 33 | Et | Me | 2-Cl-4-i-Pr—Ph | 3-pentyl | 417.2061 | 168–169 |
| 34 | Et | Me | 2-Cl-4-i-Pr—Ph | 4-heptyl | 445.2374 | 196.5–197.5 |
| 35 | H | Me | 2-Cl-4-i-Pr—Ph | 3-pentyl | 389.1762 | amorph solid |
| 36 | H | Me | 2-Cl-4-i-Pr—Ph | 4-heptyl | 417.2057 | amorph solid |
| 37 | Et | Me | 2-Cl-4-i-Pr—Ph | CH(CH$_2$OMe)Pr | | |
| 38 | Et | Me | 2-Cl-4-i-Pr—Ph | CH(CH$_2$CH=CH$_2$)$_2$ | | |

TABLE 1-continued

| Ex | R₁ | R₂ | R₃ | R₄ | (M + H)⁺ | Mp (° C.) |
|---|---|---|---|---|---|---|
| 39 | Et | Me | 2-Cl-4-i-Pr—Ph | CH(CH₂CH₂OMe)₂ | | |
| 40 | Et | Me | 2-Cl-4-i-Pr—Ph | 1-ethylbutyl | | |
| 41 | Et | Me | 2-Cl-4-i-Pr—Ph | 1-cyclopropylethyl | | |
| 42 | Et | Me | 2-Cl-4-i-Pr—Ph | 1-cyclopropylpropyl | | |
| 43 | Et | Me | 2-Cl-4-i-Pr—Ph | 1-cyclopropylbutyl | | |
| 44 | Et | Me | 2-Cl-4-i-Pr—Ph | 1-cyclopropyl-2-methoxyethyl | | |
| 45 | Et | Me | 2-Cl-4-i-Pr—Ph | 1-cyclobutylethyl | | |
| 46 | Et | Me | 2-Cl-4-i-Pr—Ph | 1-cyclobutylpropyl | | |
| 47 | Et | Me | 2-Cl-4-i-Pr—Ph | 1-cyclobutylbutyl | | |
| 48 | Et | Me | 2-Cl-4-i-Pr—Ph | 1-cyclobutyl-2-methoxyethyl | | |
| 49 | Et | Me | 2-Cl-4-i-Pr—Ph | dicyclobutylmethyl | | |
| 50 | Et | Me | 2-Cl-4-i-Pr—Ph | CH(CH₂OMe)₂ | | |
| 51 | Et | Me | 2-Cl-4-i-Pr—Ph | CH(i-Pr)Et | | |
| 52 | Et | Me | 2-Cl-4-i-Pr—Ph | CH(i-Pr)Pr | | |
| 53 | Et | Me | 2-Cl-4-i-Pr—Ph | CH(i-Pr)CH₂OMe | | |
| 54 | Et | c-Pr | 2-Cl-4-i-Pr—Ph | 3-pentyl | | |
| 55 | Et | c-Pr | 2-Cl-4-i-Pr—Ph | 4-heptyl | | |
| 56 | Et | c-Pr | 2-Cl-4-i-Pr—Ph | CH(CH₂OMe)Pr | | |
| 57 | Et | Me | 2-Cl-4-OMe-5-F—Ph | CH(CH₂CH₂OMe)₂ | | |
| 58 | Et | Me | 2-Cl-4-OMe-5-F—Ph | 1-ethylbutyl | | |
| 59 | Et | Me | 2-Cl-4-OMe-5-F—Ph | 3-pentyl | | |
| 60 | Et | Me | 2-Cl-4-OMe-5-F—Ph | 4-heptyl | | |
| 61 | Et | Me | 2-Cl-4-OMe-5-F—Ph | CH(CH₂OMe)Pr | | |
| 62 | Et | Me | 2-Cl-4-OMe-5-F—Ph | CH(CH₂CH=CH₂)₂ | | |
| 63 | Et | Me | 2-Cl-4-OMe-5-F—Ph | 1-cyclopropylethyl | | |
| 64 | Et | Me | 2-Cl-4-OMe-5-F—Ph | 1-cyclopropylpropyl | | |
| 65 | Et | Me | 2-Cl-4-OMe-5-F—Ph | 1-cyclopropylbutyl | | |
| 66 | Et | Me | 2-Cl-4-OMe-5-F—Ph | 1-cyclopropyl-2-methoxyethyl | | |
| 67 | Et | Me | 2-Cl-4-OMe-5-F—Ph | 1-cyclobutylethyl | | |
| 68 | Et | Me | 2-Cl-4-OMe-5-F—Ph | 1-cyclobutylpropyl | | |
| 69 | Et | Me | 2-Cl-4-OMe-5-F—Ph | 1-cyclobutylbutyl | | |
| 70 | Et | Me | 2-Cl-4-OMe-5-F—Ph | 1-cyclobutyl-2-methoxyethyl | | |
| 71 | Et | Me | 2-Cl-4-OMe-5-F—Ph | dicyclobutylmethyl | | |
| 72 | Et | Me | 2-Cl-4-OMe-5-F—Ph | CH(CH₂OMe)₂ | | |
| 73 | Et | Me | 2-Cl-4-OMe-5-F—Ph | CH(i-Pr)Et | | |
| 74 | Et | Me | 2-Cl-4-OMe-5-F—Ph | CH(i-Pr)Pr | | |
| 75 | Et | Me | 2-Cl-4-OMe-5-F—Ph | CH(i-Pr)CH₂OMe | | |
| 76 | Et | Me | 2,4,6-Me₃—Ph | CH(CH₂CH₂OMe)₂ | | |
| 77 | Et | Me | 2,4,6-Me₃—Ph | 1-ethylbutyl | | |
| 78 | Et | Me | 2,4,6-Me₃—Ph | 3-pentyl | | |
| 79 | Et | Me | 2,4,6-Me₃—Ph | 4-heptyl | 411.2759 | 195–195.5 |
| 80 | Et | Me | 2,4,6-Me₃—Ph | CH(CH₂OMe)Pr | | |
| 81 | Et | Me | 2,4,6-Me₃—Ph | CH(CH₂CH=CH₂)₂ | | |
| 82 | Et | Me | 2,4,6-Me₃—Ph | 1-cyclopropylethyl | | |
| 83 | Et | Me | 2,4,6-Me₃—Ph | 1-cyclopropylpropyl | | |
| 84 | Et | Me | 2,4,6-Me₃—Ph | 1-cyclopropylbutyl | | |
| 85 | Et | Me | 2,4,6-Me₃—Ph | 1-cyclopropyl-2-methoxyethyl | | |
| 86 | Et | Me | 2,4,6-Me₃—Ph | 1-cyclobutylethyl | | |
| 87 | Et | Me | 2,4,6-Me₃—Ph | 1-cyclobutylpropyl | | |
| 88 | Et | Me | 2,4,6-Me₃—Ph | 1-cyclobutylbutyl | | |
| 89 | Et | Me | 2,4,6-Me₃—Ph | 1-cyclobutyl-2-methoxyethyl | | |
| 90 | Et | Me | 2,4,6-Me₃—Ph | dicyclobutylmethyl | | |
| 91 | Et | Me | 2,4,6-Me₃—Ph | CH(CH₂OMe)₂ | | |
| 92 | Et | Me | 2,4,6-Me₃—Ph | CH(i-Pr)Et | | |
| 93 | Et | Me | 2,4,6-Me₃—Ph | CH(i-Pr)Pr | | |
| 94 | Et | Me | 2,4,6-Me₃—Ph | CH(i-Pr)CH₂OMe | | |
| 95 | Et | Me | 2,4-OMe₂—Ph | CH(CH₂CH₂OMe)₂ | | |
| 96 | Et | Me | 2,4-OMe₂—Ph | 1-ethylbutyl | | |
| 97 | Et | Me | 2,4-OMe₂—Ph | 3-pentyl | | |
| 98 | Et | Me | 2,4-OMe₂—Ph | 4-heptyl | | |
| 99 | Et | Me | 2,4-OMe₂—Ph | CH(CH₂OMe)Pr | | |
| 100 | Et | Me | 2,4-OMe₂—Ph | CH(CH₂CH=CH₂)₂ | | |
| 101 | Et | Me | 2,4-OMe₂—Ph | 1-cyclopropylethyl | | |
| 102 | Et | Me | 2,4-OMe₂—Ph | 1-cyclopropylpropyl | | |
| 103 | Et | Me | 2,4-OMe₂—Ph | 1-cyclopropylbutyl | | |
| 104 | Et | Me | 2,4-OMe₂—Ph | 1-cyclopropyl-2-methoxyethyl | | |

TABLE 1-continued

| Ex | $R_1$ | $R_2$ | $R_3$ | $R_4$ | $(M + H)^+$ | Mp (° C.) |
|---|---|---|---|---|---|---|
| 105 | Et | Me | 2,4-OMe$_2$—Ph | 1-cyclobutylethyl | | |
| 106 | Et | Me | 2,4-OMe$_2$—Ph | 1-cyclobutylpropyl | | |
| 107 | Et | Me | 2,4-OMe$_2$—Ph | 1-cyclobutylbutyl | | |
| 108 | Et | Me | 2,4-OMe$_2$—Ph | 1-cyclobutyl-2-methoxyethyl | | |
| 109 | Et | Me | 2,4-OMe$_2$—Ph | dicyclobutylmethyl | | |
| 110 | Et | Me | 2,4-OMe$_2$—Ph | CH(CH$_2$OMe)$_2$ | | |
| 111 | Et | Me | 2,4-OMe$_2$—Ph | CH(i-Pr)Et | | |
| 112 | Et | Me | 2,4-OMe$_2$—Ph | CH(i-Pr)Pr | | |
| 113 | Et | Me | 2,4-OMe$_2$—Ph | CH(i-Pr)CH$_2$OMe | | |
| 114 | Et | Me | 2-Me-4-OMe-pyrid-3-yl | CH(CH$_2$CH$_2$OMe)$_2$ | | |
| 115 | Et | Me | 2-Me-4-OMe-pyrid-3-yl | 1-ethylbutyl | | |
| 116 | Et | Me | 2-Me-4-OMe-pyrid-3-yl | 3-pentyl | | |
| 117 | Et | Me | 2-Me-4-OMe-pyrid-3-yl | 4-heptyl | 414.2506 | 124–126 |
| 118 | Et | Me | 2-Me-4-OMe-pyrid-3-yl | CH(CH$_2$OMe)Pr | | |
| 119 | Et | Me | 2-Me-4-OMe-pyrid-3-yl | CH(CH$_2$CH=CH$_2$)$_2$ | | |
| 120 | Et | Me | 2-Me-4-OMe-pyrid-3-yl | 1-cyclopropylethyl | | |
| 121 | Et | Me | 2-Me-4-OMe-pyrid-3-yl | 1-cyclopropylpropyl | | |
| 122 | Et | Me | 2-Me-4-OMe-pyrid-3-yl | 1-cyclopropylbutyl | | |
| 123 | Et | Me | 2-Me-4-OMe-pyrid-3-yl | 1-cyclopropyl-2-methoxyethyl | | |
| 124 | Et | Me | 2-Me-4-OMe-pyrid-3-yl | 1-cyclobutylethyl | | |
| 125 | Et | Me | 2-Me-4-OMe-pyrid-3-yl | 1-cyclobutylpropyl | | |
| 126 | Et | Me | 2-Me-4-OMe-pyrid-3-yl | 1-cyclobutylbutyl | | |
| 127 | Et | Me | 2-Me-4-OMe-pyrid-3-yl | 1-cyclobutyl-2-methoxyethyl | | |
| 128 | Et | Me | 2-Me-4-OMe-pyrid-3-yl | dicyclobutylmethyl | | |
| 129 | Et | Me | 2-Me-4-OMe-pyrid-3-yl | CH(CH$_2$OMe)$_2$ | | |
| 130 | Et | Me | 2-Me-4-OMe-pyrid-3-yl | CH(i-Pr)Et | | |
| 131 | Et | Me | 2-Me-4-OMe-pyrid-3-yl | CH(i-Pr)Pr | | |
| 132 | Et | Me | 2-Me-4-OMe-pyrid-3-yl | CH(i-Pr)CH$_2$OMe | | |
| 133 | Et | Me | 2,4-Me$_2$-pyrid-3-yl | CH(CH$_2$CH$_2$OMe)$_2$ | | |
| 134 | Et | Me | 2,4-Me$_2$-pyrid-3-yl | 1-ethylbutyl | | |
| 135 | Et | Me | 2,4-Me$_2$-pyrid-3-yl | 3-pentyl | | |
| 136 | Et | Me | 2,4-Me$_2$-pyrid-3-yl | 4-heptyl | | |
| 137 | Et | Me | 2,4-Me$_2$-pyrid-3-yl | CH(CH$_2$OMe)Pr | | |
| 138 | Et | Me | 2,4-Me$_2$-pyrid-3-yl | CH(CH$_2$CH=CH$_2$)$_2$ | | |
| 139 | Et | Me | 2,4-Me$_2$-pyrid-3-yl | 1-cyclopropylethyl | | |
| 140 | Et | Me | 2,4-Me$_2$-pyrid-3-yl | 1-cyclopropylpropyl | | |
| 141 | Et | Me | 2,4-Me$_2$-pyrid-3-yl | 1-cyclopropylbutyl | | |
| 142 | Et | Me | 2,4-Me$_2$-pyrid-3-yl | 1-cyclopropyl-2-methoxyethyl | | |
| 143 | Et | Me | 2,4-Me$_2$-pyrid-3-yl | 1-cyclobutylethyl | | |
| 144 | Et | Me | 2,4-Me$_2$-pyrid-3-yl | 1-cyclobutylpropyl | | |
| 145 | Et | Me | 2,4-Me$_2$-pyrid-3-yl | 1-cyclobutylbutyl | | |
| 146 | Et | Me | 2,4-Me$_2$-pyrid-3-yl | 1-cyclobutyl-2-methoxyethyl | | |
| 147 | Et | Me | 2,4-Me$_2$-pyrid-3-yl | dicyclobutylmethyl | | |
| 148 | Et | Me | 2,4-Me$_2$-pyrid-3-yl | CH(CH$_2$OMe)$_2$ | | |
| 149 | Et | Me | 2,4-Me$_2$-pyrid-3-yl | CH(i-Pr)Et | | |
| 150 | Et | Me | 2,4-Me$_2$-pyrid-3-yl | CH(i-Pr)Pr | | |
| 151 | Et | Me | 2,4-Me$_2$-pyrid-3-yl | CH(i-Pr)CH$_2$OMe | | |

Also provided herein are pharmaceutical compositions comprising compounds of this invention and a pharmaceutically acceptable carrier, which are media generally accepted in the art for the delivery of biologically active agents to animals, in particular, mammals. Pharmaceutically acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, μL for microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "α", "β", "R" and "S" are stereochemical designations familiar to those skilled in the art.

Example 1

3-(2,4-dichlorophenyl)-8-ethyl-1-methyl-7-(3-pentyl)-3,7-dihydro-1H-purine-2,6-dione A. N-(2,4-dichlorophenyl)-N'-methyl-urea A cooled (0° C.) solution of methylamine in EtOH (50 mL, 400 mmol, 8.0 M) in anhydrous THF (300 mL) was treated with 2,4-dichlorophenylisocyanate (25.0 g, 133 mmol). The cooling bath was removed and the mixture was warmed to 65° C. for 20 min. The reaction mixture was then cooled to 0° C. The solid was collected on a Buchner funnel, washed with cold ether, and dried under vacuum to afford N-(2,4-dichlorophenyl)-N'-methyl-urea (21.7 g, 74% yield) as a colorless solid: mp 213.5–214.5° C.; $^1$H NMR (300 MHz, DMSO-$d_6$) δ 8.17 (d, J=9.2 Hz, 1H), 8.11 (s, 1H), 7.55 (d, J=2.5 Hz, 1H), 7.32 (dd, J=8.8, 2.6 Hz, 1H), 6.91 (d, J=4.8 Hz, 1H), 2.65 (d, J=4.4 Hz, 3H); LRMS (APCI) m/e 259.9 [(M+H+$CH_3$CN)$^+$, calcd for $C_{10}H_{12}N_3OCl_2$, 260.0].

B. 6-amino-1-(2,4-dichlorophenyl)-3-methyl-2,4(1H,3H)-pyrimidinedione

A solution of N-(2,4-dichlorophenyl)-N'-methyl-urea (12.0 g, 54.8 mmol) in acetic anhydride (100 mL) was treated with cyanoacetic acid (5.6 g, 65.8 mmol). The reaction mixture was heated at 85° C. for 2.5 h. Additional cyanoacetic acid (0.90 g, 11.0 mmol) was added and the reaction mixture was stirred for 45 min. A third portion of cyanoacetic acid (0.45 g, 5.5 mmol) was added and the reaction mixture was stirred for 30 min. Excess acetic anhydride was distilled off under reduced pressure at a temperature not higher than 70° C. The residue was treated with 20% aqueous sodium hydroxide (95 mL) in portions. During the addition a spontaneous increase in temperature (65–70° C.) occurred. The reaction mixture was heated at 60° C. for 1 h during which time the product precipitated. The reaction mixture was then cooled to 0° C. The precipitate was collected on a Buchner funnel, washed with cold water, and dried at 55° C. under vacuum. The crude product was triturated in hot toluene (stirred for 1 h at 110° C.), and the solid was immediately collected on a Buchner funnel then dried under vacuum to afford a pale yellow solid (8.46 g, 54% yield): mp 249–251° C.; $^1$H NMR (300 MHz, DMSO-$d_6$) δ 7.89 (d, J=1.8 Hz, 1H), 7.59 (d, J=1.8 Hz, 2H), 6.44 (s br, 1H), 4.79 (s, 1H), 3.09 (s, 3H); LRMS (APCI) m/e 286.0 [(M+H)$^+$, calcd for $C_{11}H_{10}N_3O_2Cl_2$ 286.0].

C. 6-amino-1-(2,4-dichlorophenyl)-3-methyl-5-nitroso-2,4(1H,3H)-pyrimidinedione

To a suspension of the intermediate produced in Part B (8.0 g, 28.0 mmol) in $H_2O$ (65 mL) and acetic acid (3.5 mL) was added $NaNO_2$ (2.12 g, 30.8 mmol) in portions. The reaction mixture was heated at 50° C. for 2 h during which time a purple color formed indicating formation of the nitroso derivative. Additional $NaNO_2$ (2.12 g, 30.8 mmol) was added and the reaction mixture was stirred at 65° C. for an additional 2 h. Additional $NaNO_2$ (300 mg, 4.35 mmol) was added and the reaction mixture was heated at 75° C. for another 1 h. The suspension was then cooled to 0° C. The solid was collected on a Buchner funnel, washed with cold water, and dried under vacuum at 60° C. overnight to afford the nitroso derivative as a purple solid (7.78 g, 88% yield) which was used directly in the next step without further purification: mp 230–232° C.; $^1$H NMR (300 MHz, DMSO-$d_6$) δ 12.62 (s, 1H), 8.70 (s, 1H), 7.98 (s, 1H), 7.68 (s, 2H), 3.32 (s, 3H); LRMS (APCI) m/e 314.9 [(M+H)$^+$, calcd for $C_{11}H_9N_4O_3Cl_2$ 315.0].

D. 5,6-diamino-1-(2,4-dichlorophenyl)-3-methyl-2,4(1H,3H)-pyrimidinedione

To a suspension of finely ground material which was produced in Part C (7.32 g, 23.2 mmol) in 25% $NH_4OH$ (60 mL) was added in portions $Na_2S_2O_4$ (20.0 g, 116 mmol). A mildly exothermic reaction occurred. After the addition was complete, the reaction mixture was heated at 50° C. for 2.5 h. The purple color gradually disappeared. The reaction mixture was cooled to 0° C. The solid was collected on a Buchner funnel, washed with cold water, then dried under vacuum overnight at 60° C. to afford a pale green solid (6.40 g, 92% yield) which was used directly in the next step without further purification: mp 170–172.5° C.; $^1$H NMR (300 MHz, DMSO-$d_6$) δ 7.88 (d, J=2.2 Hz, 1H), 7.61–7.53 (m, 2H), 5.73 (s, 2H), 3.34 (s, 2H), 3.15 (s, 3H); LRMS (APCI) m/e 300.9 [(M+H)$^+$, calcd for $C_{11}H_{11}N_4O_2Cl_2$ 301.0].

E. 3-(2,4-dichlorophenyl)-8-ethyl-1-methyl-3,7-dihydro-1H-purine-2,6-dione

A suspension of the product from Part D (4.0 g, 13.3 mmol) in EtOH (32 mL) was treated with triethylorthopropionate (12.8 mL, 63.7 mmol). The reaction mixture was heated at reflux for 6 h during which time the product precipitated from the solution. The reaction mixture was then cooled to 0° C. to achieve complete precipitation. The solid was collected on a Buchner funnel, washed with cold ether, and dried under vacuum to give a colorless solid (2.97 g). The filtrate was concentrated and the residue was purified by column chromatography on silica gel (5% MeOH in $CH_2Cl_2$) to afford an additional 0.87 g of desired product. The total yield of desired product was 3.84 g (85% yield) as a colorless solid: mp 274.5–275.5° C.; $^1$H NMR (300 MHz, CDCl$_3$) δ 12.53 (s br, 1H), 7.61 (d, J=1.8 Hz, 1H), 7.45–7.38 (m, 2H), 3.52 (s, 3H), 2.87 (q, J=7.3 Hz, 2H), 1.38 (t, J=7.7 Hz, 3H); LRMS (APCI) m/e 339.0 [(M+H)$^+$, calcd for $C_{14}H_{13}N_4O_2Cl_2$ 339.0].

F. 3-(2,4-dichlorophenyl)-8-ethyl-1-methyl-7-(3-pentyl)-3,7-dihydro-1H-purine-2,6-dione Method A A solution of product from Part E (544 mg, 1.60 mmol) in anhydrous DMF (8 mL) was treated with finely ground $K_2CO_3$ (662 mg, 4.80 mmol). After stirring 5 min at rt, 3-methanesulfonylpentane (682 μL, 4.48 mmol) was added via syringe and the reaction mixture was heated at 80° C. for 2 h. The mixture was cooled to rt and transferred to a separatory funnel containing ether (120 mL). The organic layer was washed with water (4×15 mL), brine (15 mL), dried over MgSO$_{41}$ filtered, and concentrated. The solid residue was crystallized from hexane/ethyl acetete and collected on a Buchner funnel to give a colorless solid (508 mg). The filtrate was concentrated and the residue was purified by column chromatography on silica gel (25% ethyl acetate in hexanes) to give an additional 105 mg of product. The total yield of desired product was 613 mg (94% yield) as a colorless solid: mp 186–187° C.; $^1$H NMR (300 MHz, CDCl$_3$) δ 7.59 (d, J=2.2 Hz, 1H), 7.44–7.36 (m, 2H), 4.00–3.90 (m, 1H), 3.45 (s, 3H), 2.74 (q, J=7.7 Hz, 2H), 2.39–2.26 (m, 2H), 2.05–1.92 (m, 2H), 1.24 (t, J=7.3 Hz, 3H), 0.83 (t, J=7.3 Hz, 6H); HRMS (ESI) m/e 409.1212 [(M+H)$^+$, calcd for $C_{19}H_{23}N_4O_2Cl_2$ 409.1198].

Method B

A solution of product from Part E (100 mg, 0.295 mmol) in anhydrous THF (1.2 mL) was heated to 50° C. PPh$_3$ (120 mg, 0.594 mmol) and 3-pentanol (96 μL, 0.889 mmol) were added. After stirring 5 min, DEAD (102 μL, 0.648 mmol) was added rapidly via syringe and the reaction mixture was stirred 15 min at 50° C. The mixture was cooled to room temperature and was poured into a separatory funnel containing saturated aqueous NaHCO$_3$ (15 mL). The aqueous layer was extracted with EtOAc (3×15 mL). The combined organic layers were washed with brine, dried over MgSO$_4$, filtered, and concentrated. The residue was purified by prep plate (two 1000 μM silica gel plates, 60% ethyl acetate/40% hexanes) to afford the desired product (88 mg, 64% yield) as a colorless solid. The spectral data is identical to that reported in method A.

Example 2

3-(2,4-dichlorophenyl)-8-ethyl-7-(4-heptyl)-1-methyl-3,7-dihydro-1H-purine-2,6-dione Prepared by the method described in example 1 using the appropriate starting materials to give the desired product. colorless solid; mp 185–186° C.; HRMS (ESI) m/e 437.1532 [(M+H)$^+$, calcd for $C_{21}H_{27}N_4O_2Cl_2$ 437.1511].

Example 3

7-benzyloxymethyl-3-(2,4-dichlorophenyl)-8-ethyl-1-methyl-3,7-dihydro-1H-purine-2,6-dione Prepared by the method described in example 1 using the appropriate starting materials to give the desired product. colorless amorphous solid; HRMS (ESI) m/e 459.1011 [(M+H)$^+$, calcd for $C_{22}H_{21}N_4O_3Cl_2$ 459.0991].

Example 4

7-(1-allyl-3-butenyl)-3-(2,4-dichlorophenyl)-8-ethyl-1-methyl-3,7-dihydro-1H-purine-2,6-dione Prepared by the method described in example 1 using the appropriate starting materials to give the desired product. colorless solid, mp 145–146° C.; HRMS (ESI) m/e 433.1202 [(M+H)$^+$, calcd for $C_{21}H_{23}N_4O_2Cl_2$ 433.1198].

Example 5

3-(2,4-dichlorophenyl)-1-methyl-7-(3-pentyl)-3,7-dihydro-1H-purine-2,6-dione

Prepared by the method described in example 1 using the appropriate starting materials to give the desired product. colorless solid, mp 158–159° C.; HRMS (ESI) m/e 381.0889 [(M+H)$^+$, calcd for $C_{17}H_{19}N_4O_2Cl_2$ 381.0885].

Example 6

3-(2,4-dichlorophenyl)-7-(4-heptyl)-1-methyl-3,7-dihydro-1H-purine-2,6-dione

Prepared by the method described in example 1 using the appropriate starting materials to give the desired product. colorless amorphous solid; HRMS (ESI) m/e 409.1192 [(M+H)$^+$, calcd for $C_{19}H_{23}N_4O_2Cl_2$ 409.1198].

Example 7

3-(2,4-dichlorophenyl)-8-ethyl-7-(4-methoxybenzyl)-1-methyl-3,7-dihydro-1H-purine-2,6-dione Prepared by the method described in example 1 using the appropriate starting materials to give the desired product. It was necessary to chlorinate the aryl ring after completion of part A (example 1). The following procedure was used.

A suspension of N-(4-isopropyl)-N'-methyl-urea (39.1 g, 203 mmol) in CH$_3$CN (340 mL) was warmed to 65° C. N-chlorosuccinimide (27.1 g, 133.5 mmol) was added and the reaction mixture was heated at reflux for 5.5 h. The mixture was cooled to 0° C. The solid precipitate was collected on a Buchner funnel, washed with ether, then dried under vacuum to afford the desired product (37.37 g, 81% yield) as a colorless solid: $^1$H NMR (300 MHz, CDCl$_3$) δ 7.87 (d, J=8.1 Hz, 1H), 7.19 (d, 1.8 Hz, 1H), 7.09 (dd, J=8.4, 2.2 Hz, 1H), 6.72 (s, 1H), 5.05–5.00 (m, 1H), 2.85 (d, 3H), 2.84 (s obs, 1H), 1.21 (d, J=8.4 Hz, 6H); LRMS (APCI) m/e 453.1 [(2M+H)$^+$, calcd for C$_{22}$H$_{31}$N$_4$O$_2$Cl$_2$ 453.2].

The preparation of example 7 was completed using the method described in example 1 to give the desired product. colorless solid, mp 209–210° C.; HRMS (ESI) m/e 459.09.75 [(M+H)$^+$, calcd for C$_{22}$H$_{21}$N$_4$O$_3$Cl$_2$ 459.0990].

Example 33

3-[2-chloro-4-(isopropylphenyl)]-8-ethyl-1-methyl-7-(3-pentyl)-3,7-dihydro-1H-purine-2,6-dione Prepared by the method described in example 7 using the appropriate starting materials to give the desired product. mp 168–169° C.; HRMS (ESI) m/e 417.2061 [(M+H)$^+$, calcd for C$_{22}$H$_{30}$N$_4$O$_2$Cl 417.2057].

Example 34

3-[2-chloro-4-(isopropylphenyl)]-8-ethyl-7-(4-heptyl)-1-methyl-3,7-dihydro-1H-purine-2,6-dione Prepared by the method described in example 7 using the appropriate starting materials to give the desired product. colorless solid, mp 196.5–197.5° C.; HRMS (ESI) m/e 445.2374 [(M+H)$^+$, calcd for C$_{24}$H$_{34}$N$_4$O$_2$Cl 445.2370].

Example 35

3-[2-chloro-4-(isopropylphenyl)]-1-methyl-7-(3-pentyl)-3,7-dihydro-1H-purine-2,6-dione Prepared by the method described in example 7 using the appropriate starting materials to give the desired product. colorless amorphous solid; HRMS (ESI) m/e 389.1762 [(M+H)$^+$, calcd for C$_{20}$H$_{26}$N$_4$O$_2$Cl 389.1744].

Example 36

3-[2-chloro-4-(isopropylphenyl)]-7-(4-heptyl)-1-methyl-3,7-dihydro-1H-purine-2,6-dione Prepared by the method described in example 7 using the appropriate starting materials to give the desired product. colorless amorphous solid; HRMS (ESI) m/e 417.2057 [(M+H)$^+$, calcd for C$_{22}$H$_{30}$N$_4$O$_2$Cl 417.2057].

Example 79

8-ethyl-7-(4-heptyl)-1-methyl-3-(2,4,6-trimethylphenyl)-3,7-dihydro-1H-purine-2,6-dione Prepared by the method described in example 1 using the appropriate starting materials to give the desired product. colorless solid, mp 195–195.5° C.; HRMS (ESI) m/e 411.2759 [(M+H)$^+$, calcd for C$_{24}$H$_{35}$N$_4$O$_2$Cl 411.2760].

Example 117

8-ethyl-7-(4-heptyl)-3-(4-methoxy-2-methylpyrid-3-yl)-1-methyl-3,7-dihydro-1H-purine-2,6-dione A. 8-ethyl-7-(4-heptyl)-3-(4-methoxybenzyl)-1-methyl-3,7-dihydro-1H-purine-2,6-dione 8-ethyl-7-(4-heptyl)-3-(4-methoxybenzyl)-1-methyl-3,7-dihydro-1H-purine-2,6-dione was prepared by the method described in example 1: colorless solid, mp 120.5–121.5° C.; $^1$H NMR (300 MHz, CDCl$_3$) δ 7.56 (d, J=8.4 Hz, 2H), 6.85 (d, J=8.8 Hz, 2H), 5.22 (s, 2H), 4.15–4.04 (m, 1H), 3.78 (s, 3H), 3.39 (s, 3H), 2.78 (q, J=7.4 Hz, 2H), 2.27–2.18 (m, 2H), 1.88–1.78 (m, 2H), 1.41 (t, J=7.4 Hz, 3H), 1.25–1.00 (m, 4H), 0.88 (t, J=7.3 Hz, 6H); LRMS (APCI) m/e 825.3 [(2M+H)$^+$, calcd for C$_{46}$H$_{65}$N$_8$ 825.5].

B. 8-ethyl-7-(4-heptyl)-1-methyl-3,7-dihydro-1H-purine-2,6-dione

A solution of 8-ethyl-7-(4-heptyl)-3-(4-methoxybenzyl)-1-methyl-3,7-dihydro-1H-purine-2,6-dione in trifluoroacetic acid was heated at 100° C. in a sealed tube for 8 h. The mixture was cooled to r.t. and concentrated. The residue was transferred into a separatory funnel containing saturated aqueous NaHCO$_3$ (20 mL) and the aqueous layer was extracted with EtOAc (3×30 mL). The combined organic layers were washed with brine, dried over MgSO$_4$, filtered, and concentrated. The residue was purified by column chromatography on silica gel (5% methanol in CH$_2$Cl$_2$) to afford a colorless solid (645 mg, 91% yield): mp 152.5–153° C.; $^1$H NMR (300 MHz, CDCl$_3$) δ 12.0 (s, 1H), 4.20–4.10 (m, 1H), 3.41 (s, 3H), 2.94 (q, J=7.3 Hz, 2H), 2.33–2.19 (m, 2H), 1.94–1.83 (m, 2H), 1.42 (t, J=7.4 Hz, 3H), 1.26–1.06 (m, 4H), 0.90 (t, J=7.3 Hz, 6H); LRMS (APCI) m/e 293.1 [(M+H)$^+$, calcd for C$_{15}$H$_{25}$N$_4$O$_2$ 293.2].

C. 8-ethyl-7-(4-heptyl)-3-(4-methoxy-2-methyl-pyrid-3-yl)-1-methyl-3,7-dihydro-1H-purine-2,6-dione The solid from part B (250 mg, 0.856 mmol), 6-methoxy-2-methyl-3-pyridylboronic acid (286 mg, 1.71 mmol), Cu(OAc)$_2$ (233 mg, 1.28 mmol), and 4 A powdered molecular sieves (320 mg) were combined and treated with CH$_2$Cl$_2$ (5 mL) and pyridine (138 μL, 1.71 mmol). The reaction mixture was stirred at r.t. for two days. Additional 6-methoxy-2-methyl-3-pyridylboronic acid (286 mg, 0.856 mmol) and Cu(OAc)$_2$ (233 mg, 1.28 mmol) was added and the reaction mixture was stirred at 35° C. for an additional two days. The mixture was treated with NH$_3$ in MeOH (5 mL, 2 M) and was filtered through Celite. The filtrate was concentrated and the residue was purified by MPLC on silica gel (20% EtOAc in hexanes followed by 50% EtOAc in hexanes to recover starting material) to afford the target compound (73 mg, 21% yield) and recovered starting material (67 mg, 27% recovery). The desired product was a tan solid: mp 124–126° C.; $^1$H NMR (300 MHz, CDCl$_3$) δ 7.45 (d, J=8.5 Hz, 1H), 6.70 (d, J=8.8 Hz, 1H), 4.18–4.05 (m, 1H), 3.97 (s, 3H), 3.46 (s, 3H), 2.72 (q, J=7.7 Hz, 2H), 2.35–2.20 (m, 2H), 2.25 (s, 3 H), 1.95–1.85 (m, 2H), 1.23 (t, J=7.4 Hz, 3H), 1.20–1.05 (m, 4H), 0.94–0.87 (m, 6H); HRMS (ESI) m/e 414.2506 [(M+H)$^+$, calcd for C$_{22}$H$_{32}$N$_5$O$_3$ 414.2505].

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from $10^{-10}$–$10^{-5}$ M), 100 μl of $^{125}$I]-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 370 C for 10 min in 200 ml of buffer containing 100 mM Tris-HCl (pH 7.4 at 370 C), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$ m) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In Vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of treating a subject afflicted with a disorder characterized by over expression of corticotropin releasing factor (CRF), which method comprises administering to the mammal a pharmaceutical composition comprising a therapeutically effective amount of a compound of formula (I):

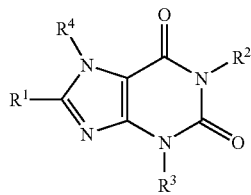

(I)

or a pharmaceutically acceptable salt form thereof, wherein:
$R^1$ is selected from the group consisting of H$C_{1-4}$ alkyl, CN, and $CF_3$;
alternatively $R^1$ is —$OR^{1a}$, wherein $R^{1a}$ is $C_1$–$C_4$ alkyl;
$R^2$ is selected from the group consisting of $C_1$–$C_6$ alkyl and $C_3$–$C_7$ cycloalkyl;
$R^3$ is selected from the group consisting of aryl and heteroaryl;
$R^4$ is selected from the group consisting of $C_{1-10}$ alkyl, $C_{2-10}$ alkenyl, $C_{3-8}$ cycloalkyl and benzyl;
$R^4$ is optionally substituted with 0–1 1-naphthalenyl groups;
alternatively $R^4$ is optionally substituted with 0–3 substituents independently selected at each occurrence from the group consisting of aryl, $C_{1-6}$ alkyl, $C_{2-8}$ alkenyl, —$OR^{10}$, —$NR^{10}R^{12}$, $CF_3$, $C_{1-4}$ alkoxy-$C_{1-4}$ alkyl and $C_{3-8}$ cycloalkyl;
$R^{10}$ is selected from the group consisting of H and benzyl;
$R^{12}$ is selected from the group consisting of H, $C_{1-4}$ alkyl, $C_{1-4}$ haloalkyl, $C_{1-4}$ alkoxy-$C_{1-4}$ alkyl, $C_{3-6}$ cycloalkyl and $C_{3-6}$ cycloalkyl-$C_{1-6}$ alkyl;
$R^{13}$ is selected from the group consisting of $C_{1-6}$ alkyl and $C_{1-4}$ haloalkyl;
aryl is phenyl optionally substituted with 0–5 substituents independently selected at each occurrence from the group consisting of phenyl, $C_{1-6}$ alkyl, —$OR^{13}$, Br, Cl, F, I and $C_{1-4}$ haloalkyl; and
heteroaryl is pyridyl optionally substituted with 0–4 substituents independently selected at each occurrence from the group consisting of $C_{1-6}$ alkyl and —$OR^{13}$.

2. The method of claim 1 wherein $R^1$ is ethyl.

3. The method of claim 1 wherein $R^1$ is methoxy.

4. The method of claim 1 wherein $R^2$ is selected from the group consisting of methyl, ethyl, propyl and cyclopropyl.

5. The method of claim 1 wherein the compound of formula (I) is selected from the group consisting of:
   3-(2,4-dichlorophenyl)-8-ethyl-1-methyl-7-(3-pentyl)-3,7-dihydro-1H-purine-2,6-dione;
   3-(2,4-dichlorophenyl)-8-ethyl-7-(4-heptyl)-1-methyl-3,7-dihydro-1H-purine-2,6-dione;
   7-benzyloxymethyl-3-(2,4-dichlorophenyl)-8-ethyl-1-methyl-3,7-dihydro-1H-purine-2,6-dione;
   7-(1-allyl-3-butenyl)-3-(2,4-dichlorophenyl)-8-ethyl-1-methyl-3,7-dihydro-1H-purine-2,6-dione;
   3-(2,4-dichlorophenyl)-1-methyl-7-(3-pentyl)-3,7-dihydro-1H-purine-2,6-dione;
   3-(2,4-dichlorophenyl)-7-(4-heptyl)-1-methyl-3,7-dihydro-1H-purine-2,6-dione;
   3-(2,4-dichlorophenyl)-8-ethyl-7-(4-methoxybenzyl)-1-methyl-3,7-dihydro-1H-purine-2,6-dione;
   3-[2-chloro-4-(isopropylphenyl)]-8-ethyl-1-methyl-7-(3-pentyl)-3,7-dihydro-1H-purine-2,6-dione;
   3-[2-chloro-4-(isopropylphenyl)]-8-ethyl-7-(4-heptyl)-1-methyl-3,7-dihydro-1H-purine-2,6-dione;
   3-[2-chloro-4-(isopropylphenyl)]-1-methyl-7-(3-pentyl)-3,7-dihydro-1H-purine-2,6-dione;
   3-[2-chloro-4-(isopropylphenyl)]-7-(4-heptyl)-1-methyl-3,7-dihydro-1H-purine-2,6-dione;
   8-ethyl-7-(4-heptyl)-1-methyl-3-(2,4,6-trimethylphenyl)-3,7-dihydro-1H-purine-2,6-dione;
   8-ethyl-7-(4-heptyl)-3-(4-methoxy-2-methylpyrid-3-yl)-1-methyl-3,7-dihydro-1H-purine-2,6-dione;
   or a pharmaceutically acceptable salt form thereof.

6. The method of claim 1 wherein said disorder is anxiety or depression.

7. The method of claim 1 wherein said disorder is irritable bowel syndrome.

* * * * *